United States Patent
Edgell et al.

(10) Patent No.: US 8,430,868 B2
(45) Date of Patent: Apr. 30, 2013

(54) AXIAL-FORCE LIMITING TORQUE WRENCH FOR USE WITH IMPLANTABLE MEDICAL DEVICES

(75) Inventors: John M. Edgell, Plymouth, MN (US); Lawrence D. Swanson, White Bear Lake, MN (US); John E. Hanson, Ham Lake, MN (US); Abhi V. Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 567 days.

(21) Appl. No.: 12/707,252

(22) Filed: Feb. 17, 2010

(65) Prior Publication Data

US 2010/0274230 A1    Oct. 28, 2010

Related U.S. Application Data

(60) Provisional application No. 61/171,960, filed on Apr. 23, 2009.

(51) Int. Cl.
*A61B 17/00* (2006.01)
*B25B 23/142* (2006.01)

(52) U.S. Cl.
USPC .................................. 606/1; 81/478

(58) Field of Classification Search ............ 81/478
See application file for complete search history.

(56) References Cited

U.S. PATENT DOCUMENTS

| | | | |
|---|---|---|---|
| 2,396,040 A * | 3/1946 | Darling | 74/126 |
| 2,797,564 A * | 7/1957 | Bonneau et al. | 464/38 |
| 3,951,154 A | 4/1976 | Hartlaub | |
| 4,346,633 A | 8/1982 | Rendl | |
| 4,461,194 A | 7/1984 | Moore | |
| 5,545,189 A | 8/1996 | Fayram | |
| 5,571,014 A * | 11/1996 | Gregory et al. | 433/141 |
| 5,697,480 A * | 12/1997 | Herbermann et al. | 192/56.32 |
| 5,746,298 A * | 5/1998 | Krivec et al. | 192/48.3 |
| 6,152,277 A | 11/2000 | Siliani et al. | |
| 6,179,063 B1 | 1/2001 | Borries et al. | |
| 6,487,943 B1 * | 12/2002 | Jansson et al. | 81/475 |
| 6,571,646 B1 | 6/2003 | Truesdell | |
| 6,776,061 B2 | 8/2004 | Schuettel et al. | |
| 2006/0016300 A1 * | 1/2006 | Bubel | 81/475 |
| 2006/0030224 A1 | 2/2006 | Degroot et al. | |
| 2006/0123958 A1 | 6/2006 | Jamnia et al. | |
| 2006/0236826 A1 * | 10/2006 | Cutler et al. | 81/475 |
| 2007/0256527 A1 * | 11/2007 | Phan | 81/475 |
| 2007/0260227 A1 * | 11/2007 | Phan | 606/1 |

FOREIGN PATENT DOCUMENTS

EP    0839612 A1    5/1998

OTHER PUBLICATIONS

PCT International Search Report and Written Opinion, mailed Jun. 2, 2010, in corresponding PCT Application Serial No. PCT/US2010/024607, 14 pages.

* cited by examiner

*Primary Examiner* — Henry M Johnson, III
*Assistant Examiner* — Scott T Luan
(74) *Attorney, Agent, or Firm* — Pauly, Devries, Smith & Deffner, L.L.C.

(57) ABSTRACT

Embodiments of the invention are related to tools for coupling leads to header assemblies for implantable medical devices, amongst other things. A wrench is configured so that if an axial force exceeding a first threshold is applied to a handle housing, then the housing handle will rotate with respect to a shaft. Other embodiments are also included herein.

18 Claims, 7 Drawing Sheets

AXIAL-FORCE LIMITING TORQUE WRENCH FOR USE WITH IMPLANTABLE MEDICAL DEVICES

This application claims the benefit of U.S. Provisional Application No. 61/171,960, filed Apr. 23, 2009, the contents of which are herein incorporated by reference.

TECHNICAL FIELD

This disclosure relates generally to implantable medical devices, and more particularly, to tools for coupling and coupling methods for use with header assemblies for implantable medical devices, amongst other things.

BACKGROUND OF THE INVENTION

Implantable medical devices (IMDs) are commonly used to provide treatment to patients. Implantable medical devices can include cardiac rhythm management devices and neurological stimulation devices, amongst others. Some types of implantable medical devices deliver electrical stimuli to a target tissue via a lead wire ("stimulation lead") or catheter having one or more electrodes disposed in or about the target tissue. The stimulation lead is frequently connected to a pulse generator housing via a structure commonly referred to as a header assembly. The header assembly serves to provide fixation of the proximal end of the stimulation lead and electrically couples the stimulation lead with the pulse generator.

During the procedure of implanting the implantable medical system, the stimulation leads are generally introduced through a major vein (typically the subclavian vein) in the upper chest and into the heart with the help of imaging devices. The distal ends of the stimulation leads include electrodes and transvenously pass to the heart. Once the stimulation leads are in the proper position, they are coupled to the pulse generator via the header assembly. Specifically, the proximal ends of the stimulation leads are inserted into ports in the header assembly and then secured in place, typically with a set screw.

A specially adapted torque wrench is used by the surgeon to screw each set screw into position. For leads with two electrodes, one set screw presses a tip electrode into its contact within the header assembly while another set screw presses a ring electrode into its contact within the header assembly. The torque wrench is designed to ensure that the proper amount of force is applied to the set screw. If a larger than necessary force is applied, the outer housing of the torque wrench rotates and ratchets against an inner component. The ratcheting action provides tactile and audible feedback to the surgeon that the set screw has been sufficiently tightened.

SUMMARY OF THE INVENTION

Embodiments of the invention are related to header assemblies for implantable medical devices, amongst other things. In an embodiment the invention includes a medical device including a header assembly housing.

In one embodiment, a wrench for coupling a set screw to a medical device includes a handle housing and a shaft that has an interface end that is configured to be received in a set screw depression defined on a head of a set screw. The shaft defines an axis of the wrench. The wrench is configured so that if an axial force exceeding a first threshold is applied to the handle housing, then the housing handle will rotate with respect to the shaft.

In another embodiment, a system for coupling a set screw to a medical device includes a header assembly housing. The header assembly housing includes a dielectric material, defines a set screw receptacle, and is configured to receive a set screw for securing a lead to an electrode. The system further includes a set screw that has a head defining a depression and a wrench. The wrench includes a handle housing and a shaft having an interface end that is configured to be received in the set screw depression. The shaft defines an axis. The wrench is configured so that if an axial force exceeding a first threshold is applied to the handle housing, then the handle housing will rotate with respect to the shaft.

In another embodiment, a method for coupling a set screw to a medical device includes the steps of providing a set screw comprising a head defining a depression, and providing a wrench including a handle housing and a shaft. The shaft includes an interface end that is configured to be received in the set screw depression and defines an axis. The wrench is configured so that if an axial force exceeding a first threshold is applied to the handle housing, then the handle housing will rotate with respect to the shaft. The method further includes the steps of positioning the set screw within an opening in a medical device, placing the interface end of the wrench in the set screw depression, and rotating the wrench.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

During the procedure of implanting a medical device, such as a pacemaker or an implantable cardioverter-defibrillator, stimulation leads are generally introduced through a major vein in the upper chest and into the heart. Once the leads are in the proper position, they are coupled to the pulse generator via the header assembly. Specifically, the proximal ends of the stimulation leads are inserted into ports in the header and then secured in place using set screws. However, it is possible for the screw to get stuck when being threaded into the connector.

If the user angles the wrench compared to an axis of the set screw, and if the user also applies a threshold axial force to the wrench, then the set screw can become stuck in the connector block. If the screw becomes stuck, then cross-threading of the set screw may occur.

Embodiments herein provide tactile feedback to the user of the torque wrench that an inappropriate amount of axial force is being applied to the set screw. Embodiments herein also can include systems and devices to limit axial forces applied to the set screw. Additional embodiments can also be configured to limit torque applied to the set screw, and provide tactile feedback when an inappropriate amount of torque is being applied to the set screw.

A wrench consistent with the technology disclosed herein is configured such that if an axial force exceeding a first threshold is applied to the handle housing, then the housing handle will rotate with respect to the shaft. Upon application of axial forces exceeding a first threshold, the housing handle disengages from the shaft of the wrench such that the handle housing rotates independently of the shaft.

The wrench can further be configured such that if torque exceeding a second threshold is applied to the handle housing, then the handle housing will rotate with respect to the shaft. A first slip surface is coupled to the handle housing, and a second slip surface is coupled to the shaft. The slip surfaces mutually engage except that when the applied torque exceeds a second threshold, the first slip surface disengages from the second slip surface such that the housing rotates independently of the shaft.

Various aspects of exemplary embodiments will now be described in greater detail.

Figure 1:
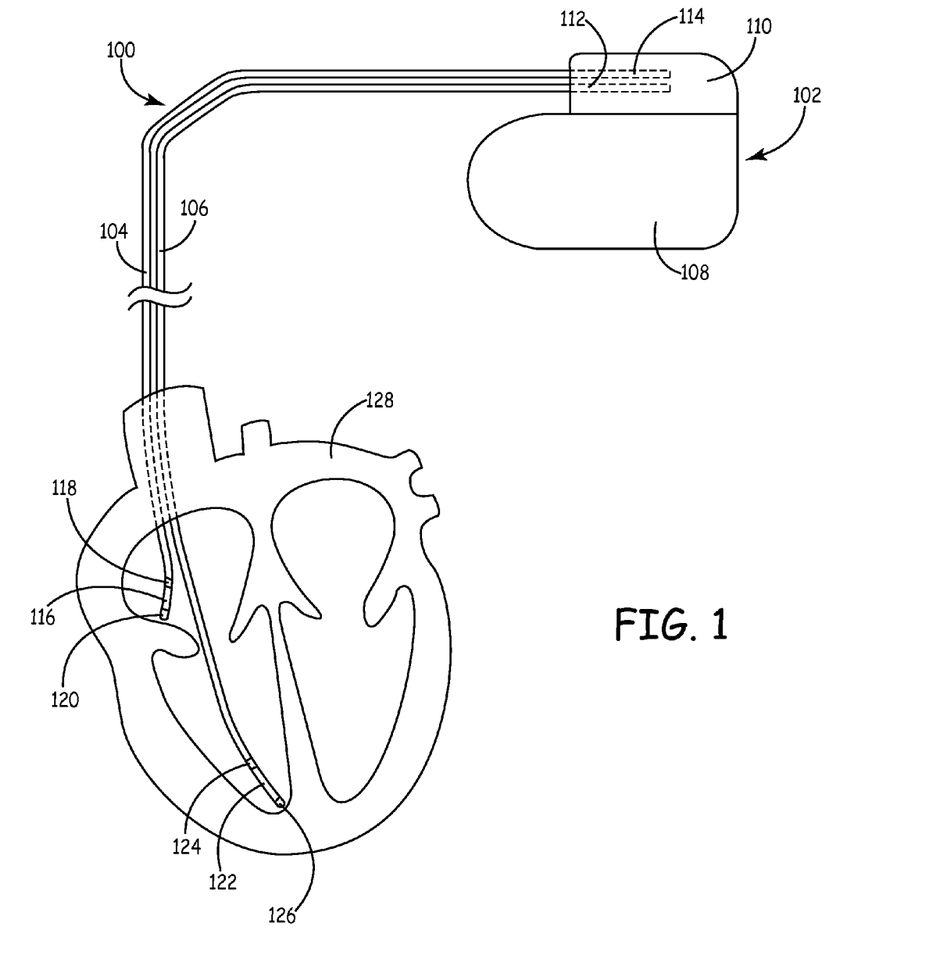
FIG. 1 is a schematic view of an implantable medical device system in accordance with an embodiment.

FIG. 1 is a schematic view of an implantable medical system 100 shown in conjunction with a heart 128. Electrical stimulation leads 104, 106 electrically couple a pulse generator 102 with the heart 128. Distal ends 116, 122 of the electrical stimulation leads 104, 106 have one or more electrodes 118, 120, 124, 126, which are disposed within the heart 128. Connector pins (not shown in this view) on the proximal ends of the electrical stimulation leads 104, 106 are disposed within port apertures 112, 114 defined by the header assembly 110. During implantation, the connector pins on the proximal ends of the leads 104, 106 are inserted into port apertures 112, 114 and into connector blocks (not shown in this view) and then secured in place, such as with a set screw.

The header assembly 110 is electrically coupled to the pulse generator housing 108. Typically, wires made from a conductive material pass from the pulse generator housing 108 to the connector blocks within the header assembly.

In operation, the pulse generator 102 may generate pacing pulses and/or therapeutic shocks which are delivered through the header assembly 110, through the leads 104, 106, and to the heart 128. In many embodiments, the leads 104, 106 include a material that is electrically conductive in order to deliver the pacing pulses or therapeutic shocks.

Figure 2:
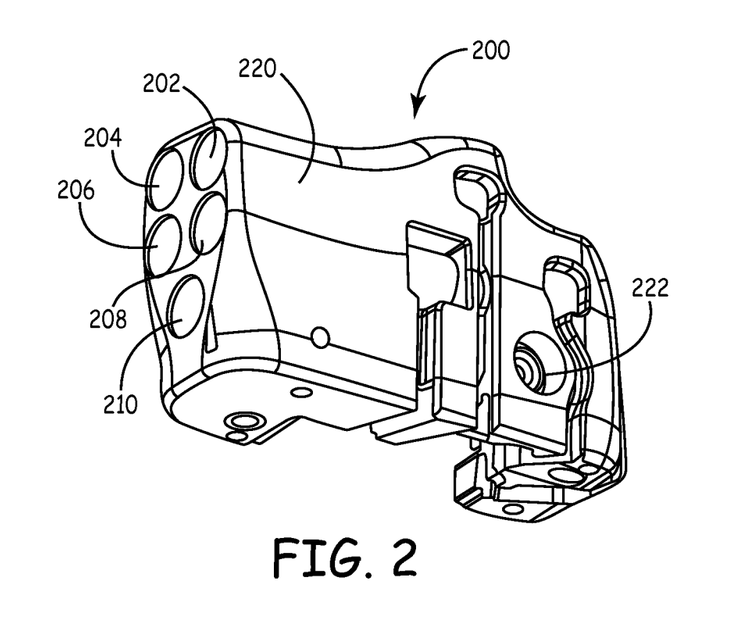
FIG. 2 is a schematic view of a header assembly in accordance with an embodiment.

FIG. 2 is a schematic view of a header assembly 200 in accordance with an embodiment. The header assembly 200 provides fixation of the proximal ends of the stimulation leads and facilitates electrical communication between electrical components within the pulse generator housing and the electrical stimulation leads in the heart. The header assembly 200 includes a header assembly housing 212 that defines multiple port apertures 202, 204, 206, 208, 210 that are configured to receive a connector pin of an electrical stimulation lead. Though there are five port apertures depicted in FIG. 2, it will be appreciated that embodiments within the scope herein can include a greater or less number of port apertures. For example, in some embodiments the header assembly can include at least one and at most twenty port apertures.

At least a portion of a connection electrode can be exposed within each port aperture 202, 204, 206, 208, 210 such that at least a portion of each proximal end of each stimulation lead is electrically coupled to its respective connection electrode upon securing the proximal end of each stimulation lead within a port aperture 202, 204, 206, 208, 210. Each connection electrode can be electrically coupled with electrical components within the pulse generator housing such that stimulation leads are electrically coupled to such electrical components upon coupling to a connection electrode. It is also possible for a single port aperture to include two, three or more multiple connection electrodes arranged along the length of the port aperture.

The header housing 220 can be made of a dielectric material (electrical insulator). Exemplary dielectric materials can include various polymers and glasses, amongst others. A specific example is TECOTHANE® brand polyurethane polymer, commercially available from Lubrizol Advanced Materials, Inc., Wilmington, Mass.

The header housing 220 can be formed through a molding process. However, it will be appreciated that the header housing 220 can also be formed in other ways. In multiple embodiments the header housing 220 is at least partially translucent such that the location of the connector pin of an electrical stimulation lead can be viewed. Such embodiments allow visualization of insertion of the connector pin of an electrical stimulation lead into the header assembly housing. In some embodiments, the header assembly housing 220 is completely translucent.

Figure 3:
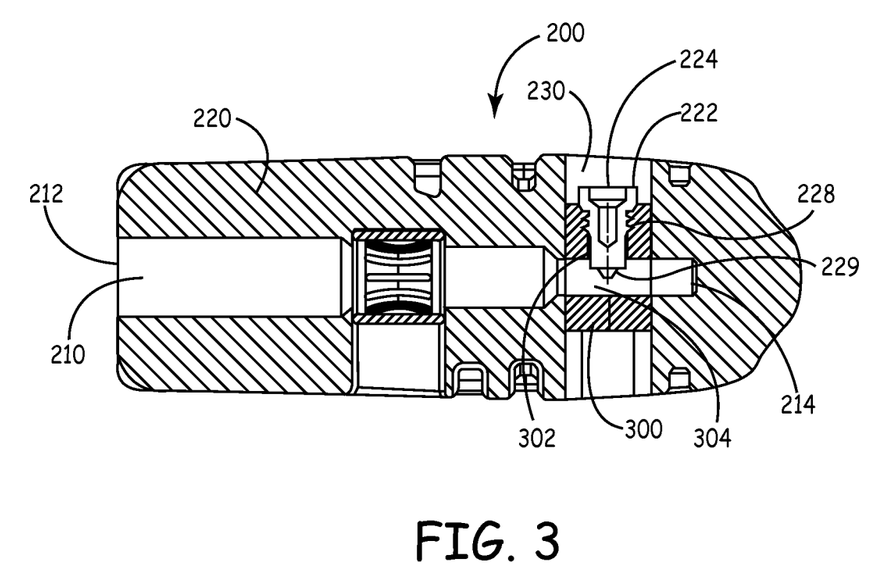
FIG. 3 is a cross-sectional view of the header assembly of FIG. 2

FIG. 3 is a cross-sectional view of the header assembly of FIG. 2, through a first port aperture 210 that can be representative of each of the port apertures 202, 204, 206, 208, 210 depicted in FIG. 2. The port aperture 210 has a first end 212 and a second end 214, where the first end 212 is the circular opening of the port aperture 210 defined by the header assembly housing 220 and the second end 214 is opposite end of the length of the port aperture 210. When connecting a stimulation lead to the header assembly 200, the tip of a connector pin of an electrical stimulation lead enters the first end 212 of the port aperture 210 and progresses to the second end 214 of the port aperture 210.

The proximal end of a stimulation lead is secured within a port aperture 210 with a set screw 222. A set screw receptacle 230 is defined by the header housing 220. A set screw 222 is positioned in a set screw receptacle 230 of the header assembly 200. A threaded shaft 228 of the set screw 222 passes through a portion of the header assembly 200 within the set screw receptacle 230 and a distal end 229 of the set screw 222 presses the proximal end of the stimulation lead into physical and electrical contact with an electrode on the interior of the header assembly 200, where the proximal end of the stimulation lead can at least partially comprise an electrode. The set screw includes a set screw depression 224 for receiving an end of a wrench.

In various embodiments, a connector block 300 is an electrode that couples with the set screw 222 to physically secure the proximal end of a stimulation lead and electrically couple the stimulation leads with the pulse generator. The connector block 300 defines threaded aperture 302 that is configured to receive the set screw 222 and a pin aperture 304 that is configured to receive the proximal end of the stimulation lead. The pin aperture 304 defined by the connector block 300 substantially aligns with the port aperture 210 of the header housing 220. Likewise, the connector block 300 is also positioned within the header assembly such that the set screw receptacle 230 of the header assembly substantially aligns with the threaded aperture 302. The connector block 300 is described in more detail in the description of FIG. 4, below.

Figure 4:
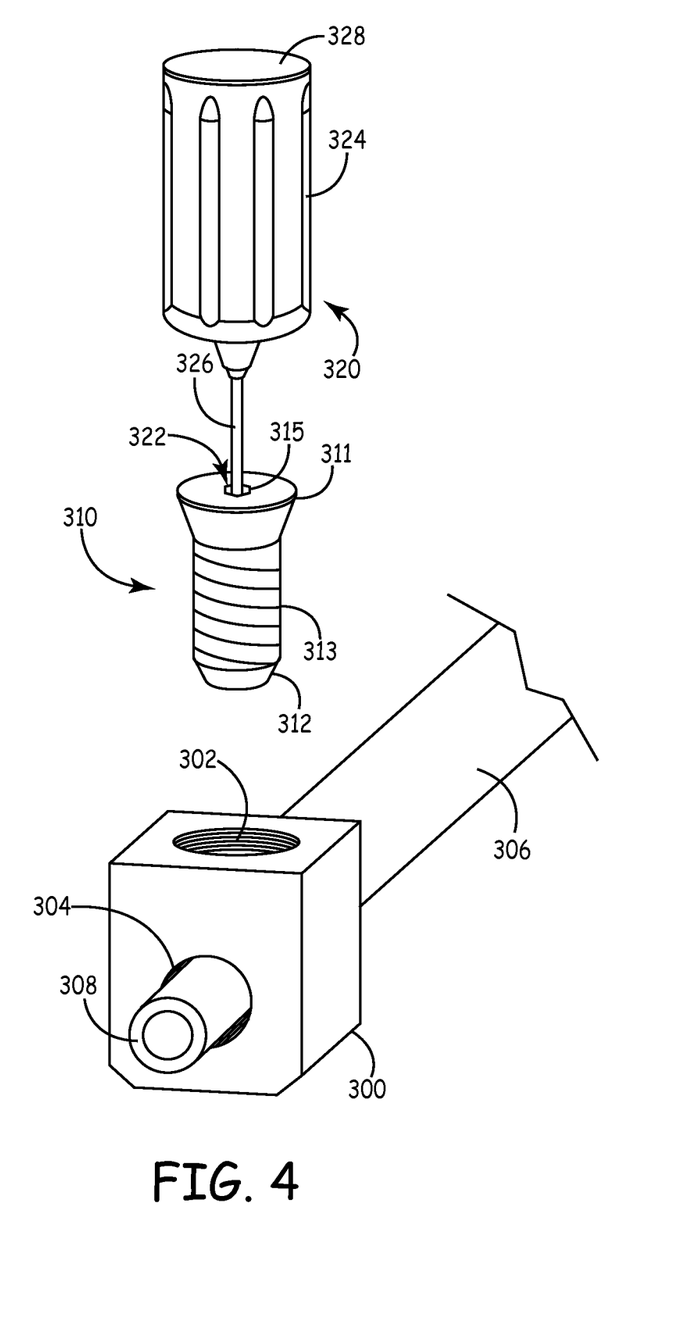
FIG. 4 is a schematic view of a stimulation lead interfacing with a connector block in accordance with an embodiment.

FIG. 4 depicts the connector block 300 of FIG. 3 defining a threaded aperture 302 and also defining a pin aperture 304. A stimulation lead 306 interfaces with the connector block 300 in accordance with an embodiment. A connector pin 308 on the proximal end of the stimulation lead 306 is shown disposed within the pin aperture 304 defined by the connector block 300. The threaded aperture 302, as defined by the connector block 300, is configured to receive a fastener, such as a set screw 310, that can secure the connector pin 308 within the pin aperture 304 of the connector block 300.

The connector block 300 can be machined, die casted, molded, or the like, and constructed from a conductive material such as copper, stainless steel, titanium, silver, or the like. The connector block 300 is generally disposed within the header assembly, such as the header assembly depicted in FIG. 2-3. In some embodiments, the connector block 300 is inserted into the header assembly housing through an insert molding process. The connector block 300 is positioned within the header assembly such that the pin aperture 304 of the connector block substantially aligns with a port aperture of the header housing. Likewise, the connector block 300 is also positioned within the header assembly such that the set screw receptacle 230 of the header assembly substantially aligns with the threaded aperture 302 of the connector block 300.

A set screw 310 is configured to be positioned in a set screw receptacle of the header assembly as described in the discussion of FIGS. 2 and 3, above. A threaded shaft 313 of the set screw 310 passes through a portion of set screw receptacle opening defined by the header housing, and enters the threaded aperture 302 defined by the connector block 300. The interface end 312 (distal end) of the set screw 310 interfaces with the threaded aperture 302 of the connector block 300 and is progressed into the connector block 300. The set screw 310 is progressed to contact the proximal end of the stimulation lead within the header, where the electrode can be a connector pin 308 and is further progressed to secure the connector pin 308 into physical and electrical contact with the electrode on the interior of the header assembly 200. In one embodiment, a connector block 300 physically fixes the proximal end of a stimulation lead and electrically couples the stimulation leads with the pulse generator.

With further reference to FIG. 4, wrench 320 is used to progress the set screw 310 into the connector block 300. The wrench 320 is manually rotated while an interface end 322 of a shaft tip 326 of the wrench 320 engages the set screw depression 315 to transfer torque from the wrench 320 to the set screw 310. In at least one embodiment the set screw depression 315 is hexagonally shaped. Likewise, in such an embodiment, the interface end 322 of the wrench 320 is also hexagonally shaped. The set screw depression 315 and interface end 322 of the wrench 320, however, can have a variety of shapes that allow engagement of the set screw 310 by the interface end 322 of the wrench 320. The set screw 310 can then be coupled to the device, or, in this particular embodiment, a connector block 300 within a header assembly.

The wrench 320 is broadly configured to limit axial forces applied to the set screw 310. The wrench 320 can also be configured to provide feedback to the user as the axial force approaches an undesirable level. The wrench 320 can also be configured to limit torque applied to the set screw 310. In the current embodiment the wrench 320 is configured such that if an axial force exceeding a first threshold is applied to the handle housing 324, then the housing handle 324 will rotate with respect to the shaft. In some embodiments, the wrench 320 is further configured such that if torque exceeding a second threshold is applied to the handle housing 324, then the handle housing 324 will rotate with respect to the shaft.

The shaft tip 326 defines at least a portion of an axis of the wrench 320. The axis defined by the shaft can be the axis of rotation of the wrench 320. In some embodiments the shape of the cross section of portions of the shaft tip 326 varies from the portion of the shaft tip 326 defining the interface end 322. In one embodiment, the shaft tip 326 is generally cylindrical except that a portion near the interface end is hexagonal.

The wrench 320 also has a handle housing 324 that is used to manually position the interface end 322 of the wrench 320, and rotate the wrench 320, thereby transferring torque to the set screw 310. The handle housing 324 shares an axis of rotation with the entire wrench 320 in various embodiments. The handle housing 324 can have a generally cylindrical shape, such as in the current embodiment, and have a cap 328 disposed on the top end of the handle housing 324 that substantially covers an opening defined by the handle housing 324.

The handle housing 324 could have a variety of other shapes and sizes, however. Generally the handle housing 324 is substantially hollow or defines an interior opening for internal components of the wrench 320 which will be further described below in the discussion of FIG. 5.

The wrench 320 is configured, in multiple embodiments, such that if an axial force exceeding a first threshold is applied to the handle housing 324, then the handle housing 324 will rotate with respect to the shaft tip 326. In some embodiments, when the axial force reaches an axial force warning threshold, then feedback is provided to the user. One example of feedback to the user is the axial movement of the handle housing with respect to the shaft tip. The user will feel the handle housing moving axially, but will still be able to turn the screw.

In use, the wrench 320 limits the amount of axial force that is applied to the set screw 310 to below a first threshold. In an embodiment the first threshold can be at least 1 pound (0.5 kg). In an embodiment the first threshold can be at least 2.5 pounds (1.1 kg). In an embodiment the first threshold can be at most 15 pounds (6.8 kg). In an embodiment the first threshold can be at most 10 pounds (4.5 kg). When the axial force applied to the set screw 310 exceeds the first threshold, the wrench 320 no longer transfers torque to the set screw 310 and the handle housing 324 disengages from the rest of the wrench 320 and spins freely.

Various wrench structures 320 consistent with the technology disclosed herein can incorporate an "axial force warning threshold" that is lower than the first threshold, at which point the wrench provides tactile feedback when the axial force applied to the set screw 310 is above the axial force warning threshold and below the first threshold. Tactile feedback can include slight compression of the handle housing 324 relative to the wrench shaft tip 326.

In an embodiment the axial force warning threshold can be at least 0.7 pound (0.7 kg) or at least 1 pound (0.5 kg). In an embodiment the axial force warning threshold can be at least 2.5 pounds (1.1 kg). In an embodiment the axial force warning threshold can be at most 15 pounds (6.8 kg). In an embodiment the axial force warning threshold can be at most 10 pounds (4.5 kg). In an embodiment the axial force warning threshold can be at most 8 pounds (3.6 kg).

Likewise, the wrench 320 can also limit the amount of torque that is applied to a set screw 310 in certain embodiments. If the torque applied to the wrench 320 is beyond a second threshold, then the handle housing 324 rotates with respect to the wrench shaft tip 326. In an embodiment the second threshold can be at least 10 inch-ounces (7.2 meter-grams). In an embodiment the second threshold can be at least 13 inch-ounces (9.36 meter-grams). In an embodiment the second threshold can be at most 20 inch-ounces (14.4 meter-grams). In an embodiment the second threshold can be at most 18 inch-ounces (12.96 meter grams). It at least one embodiment the second threshold is about 15 inch-ounces (10.8 meter-grams).

When the torque applied to the set screw 310 exceeds the second threshold, the wrench 320 no longer transfers torque to the set screw 310, and the handle housing 324 can rotate with respect to the shaft of the wrench. Various wrench structures 320 consistent with the technology disclosed herein can incorporate an "torque force warning threshold" that is lower than the second threshold, at which point the wrench 320 provides tactile feedback when the torque applied to the set screw 310 is above the torque force warning threshold and below the first threshold. Tactile feedback can include vibrations or other motions of the handle housing 324.

Figure 5:
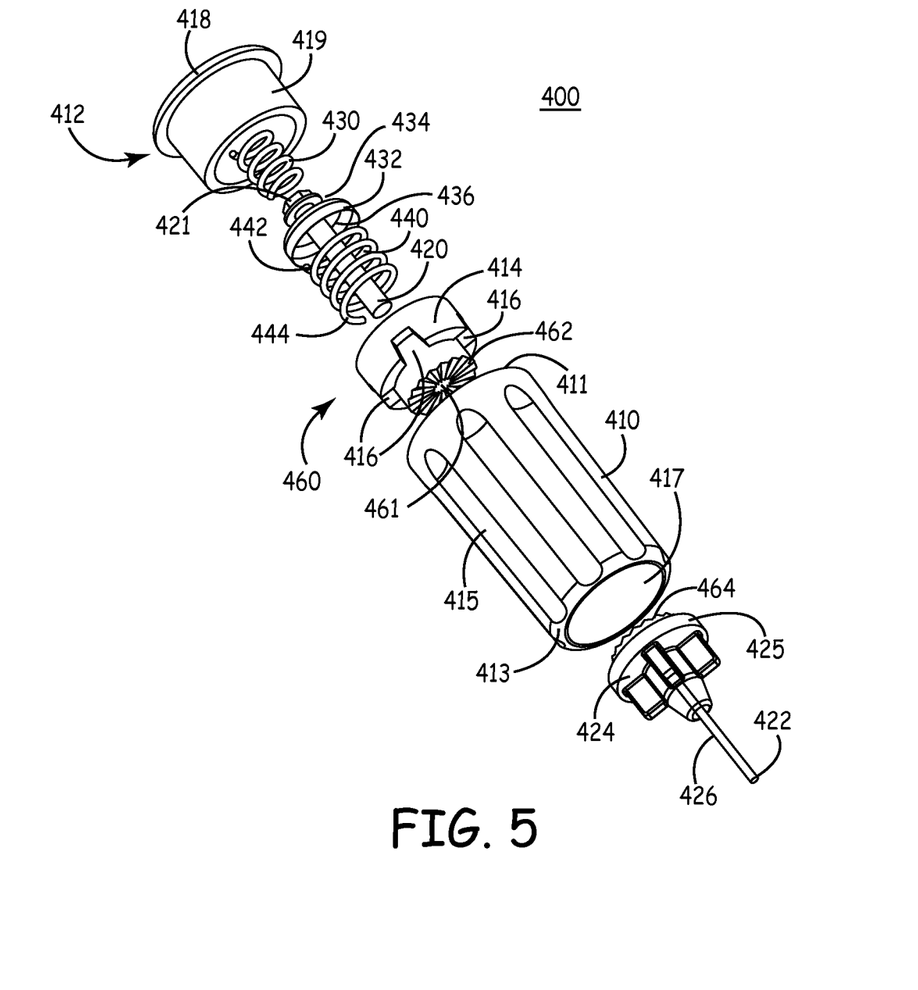
FIG. 5 is an exploded perspective view of the axial-force limiting torque wrench in accordance with the embodiment of FIG. 4.

FIG. 5 is an exploded perspective view of the axial-force limiting torque wrench in accordance with the wrench embodiment of FIG. 4. The wrench 400 has a handle housing 410 with an end cap 412 disposed on a first end 411 and a shaft tip 426 is disposed on a second end. The interface end 422 defined by the shaft tip 426 is configured to be received by a depression in a screw head. A first spring 430 is positioned between the end cap 412 and a first side 434 of an internal spring cap 432. A second spring 440 is positioned between a second side 436 of the internal spring cap 432 and a slip component 460. An internal shaft 420 is received by an opening defined by the internal spring cap 436, an opening defined by the slip component 460, and a shaft mid-section 424. The shaft mid-section 424 also receives the shaft tip 426.

As mentioned above, the handle housing 410 has a first end 411 and second end 413 and defines an opening 417 to receive various components of the wrench 400. The handle housing 410 can have a variety of shapes and sizes, and in the current embodiment is generally a cylinder that defines multiple grooves 415 along the length of the cylinder. Such grooves 415 can provide a grasping surface. In the current embodiment the opening 417 is cylindrical.

The end cap 412 is disposed in the first end 411 of the handle housing 410. The end cap 412 defines a top plate 418 coupled to a hollow cylinder 419. The outer surface of the cylinder 419 frictionally engages the inner surface of the handle housing 410 and provides a surface against which the first spring pushes. The top plate 418 is a circular portion of solid material that isolates components within the handle housing 410 from the environment outside the handle housing 410. The cylinder 419 can have a variety of other shapes, as well, and will have a shape that at least partially engages the opening 417 of the handle housing 410 on the first end 411.

The internal spring cap 432 is a disk that defines an opening to receive the internal shaft 420, and has a flange extending from the perimeter of the disk. The flange extends perpendicularly from the surface of the disk. The internal spring cap 432 can have a variety of positions, but in the current embodiment is pushed against the shaft head 421 by the second spring 440.

The internal shaft 420 is received by an opening defined by the internal spring cap 436, an opening defined by a slip component 460, and a recess in the shaft mid-section 424. The internal shaft 420 is fixed to the shaft mid-section 424 and cannot rotate with respect to the shaft midsection. The internal shaft 420 defines an axis of rotation of the wrench 400. The internal shaft 420 includes a cylinder and a shaft head 421 that is larger than the diameter of the cylinder. In one embodiment, the internal shaft 420 is a threaded bolt.

A shaft of the wrench is made up of three components that do not rotate with respect to each other: the shaft tip 426, the shaft mid-section 424 and the internal shaft 420. In one embodiment, the shaft tip is secured in an opening in a first side of the shaft mid-section by being molded into the shaft mid-section. It is also possible for the shaft tip to have a threaded connection or be secured with adhesive or other means. In one embodiment, the internal shaft 420 is secured into an opening in a second side of the shaft mid-section with a threaded connection. It is also possible for the internal shaft to be further secured or only secured with adhesive or other means. It is also possible for the internal shaft to be molded into position.

The slip component 460 is at least partially cylindrical in shape and is configured to be received by the handle housing 410. The slip component 460 defines a central opening 461 that receives the internal shaft 420. The slip component 460 can rotate with respect to the internal shaft 420. The slip component 460 is substantially co-axial with the handle housing 410 and the internal shaft 410.

The slip component also defines a first mating structure 414 that interacts with a second mating structure on the interior of the handle housing 410. In the embodiment shown in the figures, the first mating structure 414 is made up of four evenly spaced tapered notches 416. In this embodiment, the corresponding second mating structure on the interior of the handle housing is made up of four evenly spaced tapered protrusions that fit within the tapered notches 416. The second mating structure will be illustrated and further discussed with reference to FIGS. 8-11.

When the first and second mating structure are engaged with each other, the handle housing 410 and the slip component 460 rotate together, so that the rotation of the handle housing will cause rotation of the slip component. The rotation of the slip component will in turn cause rotation of the shaft of the wrench. But if an axial force that exceeds a first threshold is applied to the wrench, the first spring is compressed, causing the handle housing to move axially with respect to the slip component, and causing the tapered notches and tapered protrusions to be out of alignment with each other. As a result, the rotation of the handle housing does not cause rotation of the slip component or in turn rotation of the shaft.

The first and second mating structure can alternatively be made up of other configurations of mating structures that can engage or lock together in a first position and can also be disengaged from each other by the axial movement of one of the structures.

In one embodiment, another structure on the slip component is a first slip structure 462, which is configured to engage with an end of the shaft mid-section 424. The shaft mid-section 424 is disposed partially within a second end 413 of the handle housing 410 and is generally co-axial with the internal shaft 420 and the handle housing 410. In the current embodiment the shaft mid-section 424 has a first side that defines an opening that receives the shaft tip 426 of the wrench 400. The shaft mid-section 424 has a second side that is configured to be received by the handle housing 410 of the wrench 400. The first side defines a cylindrical opening, the inside surface of which contacts the shaft tip 426. The second side defines an outer perimeter surface 425 of a cylinder that is received by the opening 417 of the handle housing 410. The shaft mid-section 424 is able to rotate relative to the handle housing.

The second side of the shaft mid-section 424 is coupled to the internal shaft 420 and defines a second slip structure 464. The first slip structure 462 and second slip structure 464 generally fit together and rotate together except when torque applied to the handle housing 410 exceeds the second threshold. In this case, then the first slip structure 462 disengages from the second slip structure 464 on the shaft mid-section 424, allowing the handle housing 410 to rotate with respect to the internal shaft 420.

In at least one embodiment the first and second slip structures 462, 464 have mating teeth structures. Such a configuration provides tactile feedback when the torque applied to the handle housing 410 approaches and is above the second threshold. Tactile feedback can include motion resulting from the rotation of the first slip structure 462 against the second slip structure 464. As the torque approaches the second threshold, the sloped surfaces of the mating teeth structures slide against each other in opposite directions. If the torque continues to increase, the teeth disengage from each other and the tips of the teeth bump against each other as the slip component rotates with respect to the shaft housing, causing a clicking noise and a vibration. Many different mating structures are possible for the first and second slip structures 462, 464.

Figure 6:
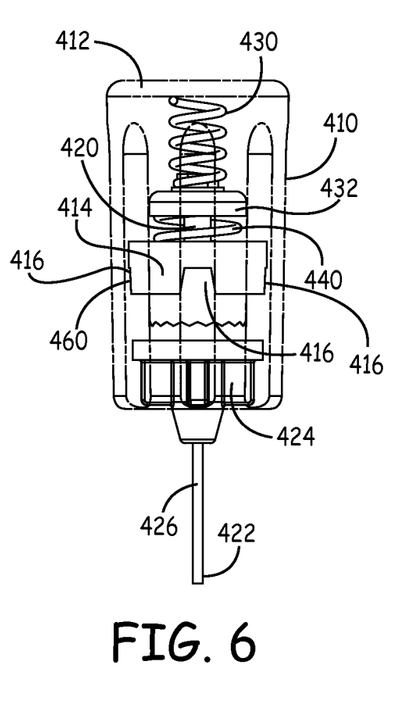
FIG. 6 is a view of the interior components of the axial-force limiting torque wrench in a first position, in accordance with the embodiment of FIG. 4.
Figure 7:
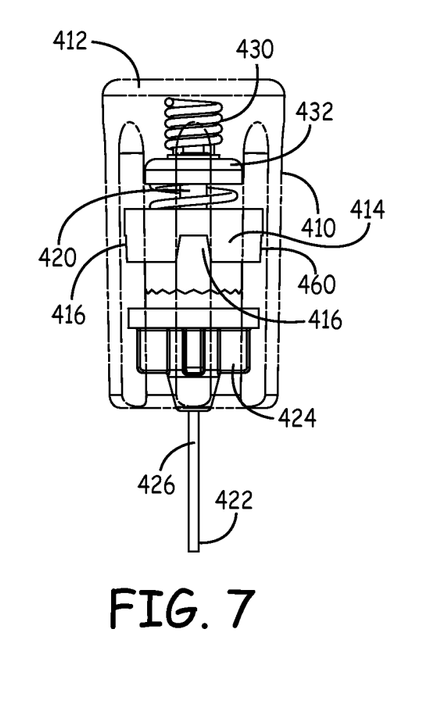
FIG. 7 is a view of the interior components of the axial-force limiting torque wrench in a second position, in accordance with the embodiment of FIG. 4.

FIGS. 6 and 7 are views of the interior components of wrench with the handle housing and end cap shown in dashed lines, in first and second positions, respectively. In FIG. 6 there is no axial force exerted on the handle housing 410, and in FIG. 7 there is force exerted on the handle housing 410 that is greater than the first threshold. Where the interface end 422 is in contact with another structure, such force is transferred from the interface end 422 of the wrench 400, through the shaft mid-section 424, internal shaft 420, and the internal spring cap 432, which causes the first spring 430 to compress against the end cap 412. When the first spring 430 compresses, the first mating structure 414 disengages from a second mating structure within the handle housing 410.

Figure 8:
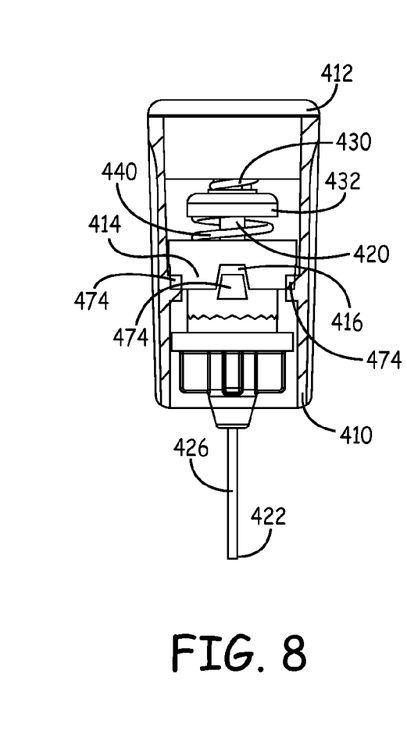
FIG. 8 is a cut-away view of the handle housing and a front view of the other components of the axial-force limiting torque wrench in a first position, in accordance with the embodiment of FIG. 4.
Figure 9:
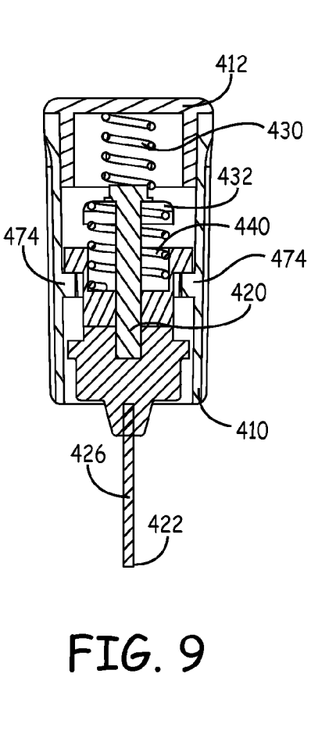
FIG. 9 is a cross-sectional view of the axial-force limiting torque wrench in a first position, in accordance with the embodiment of FIG. 4.
Figure 10:
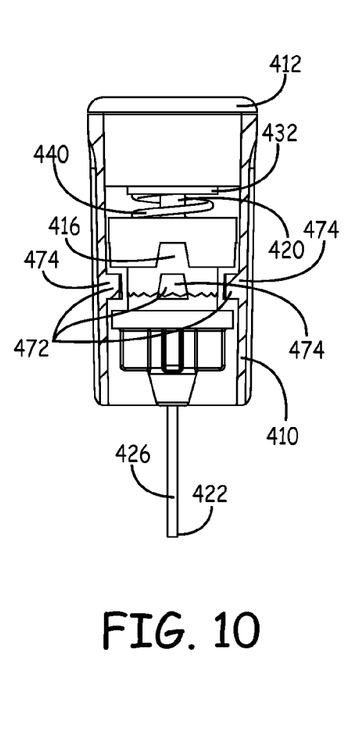
FIG. 10 is a cut-away view of the handle housing and a front view of the other components of the axial-force limiting torque wrench in a second position, in accordance with the embodiment of FIG. 4.
Figure 11:
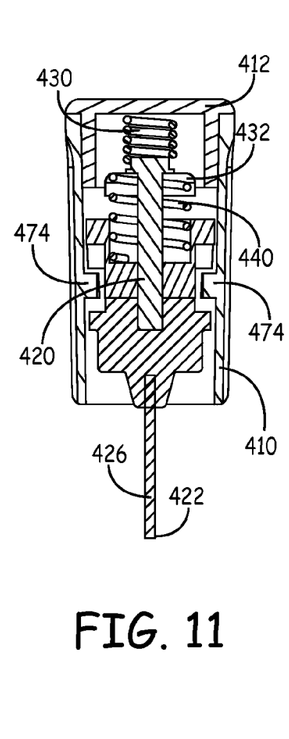
FIG. 11 is a cross-sectional view of the axial-force limiting torque wrench in a second position, in accordance with the embodiment of FIG. 4.

FIGS. 8-11 are best understood when viewed together. FIG. 8 and FIG. 9 depict the axial-force limiting torque wrench in a first position, and FIG. 10 and FIG. 11 depict the axial-force limiting torque wrench in a second position. FIG. 8 and FIG. 10 are cut-away views of the handle housing and front views of the interior components of the axial-force limiting torque wrench, where the exterior portion of the handle housing closest to the viewer has been removed, but the interior structures of the handle housing closes to the viewer are shown, namely the protrusion 474. FIG. 9 and FIG. 11 are cross-sectional views of the axial-force limiting torque wrench.

The position of the wrench 400 depicted in FIG. 8-9 is consistent with the wrench in a neutral state, with no axial forces exerted on the handle housing 410. That is, the first spring 430 is uncompressed and thus the first mating structure (made up of notches 416) engages the second mating structure (protrusions 474) on the interior of the handle housing. The wrench 400 is configured so that if an axial force exceeding a first threshold is applied to the handle housing 410, then the handle housing 410 will rotate with respect to the internal shaft 420. Thus, the position of the wrench depicted in FIG. 9 and FIG. 11 is consistent with the wrench in a compressed state, with axial forces exerted on the handle housing 410 greater than the first threshold. That is, the first spring 430 is compressed and thus the first mating structure (notches 416) disengages from the second mating structure (protrusions 474).

It will be appreciated that the first mating structure and the second mating structure can have a variety of configurations, and generally mate except when an axial force applied to the handle housing 410 exceeds a first threshold. As described above, the first mating structure 414 defines at least one tapered notch 416 and the second mating structure 472 has at least one protrusion 474. In one embodiment, the first mating structure 414 defines at least two tapered notches 416 and the second mating structure 472 has at least two protrusions 474. In another embodiment, the first mating structure 414 defines at least three tapered notches 416 and the second mating structure 472 has at least three protrusions 474. In another embodiment, the first mating structure 414 defines four tapered notches 416 and the second mating structure 472 comprises four protrusions 474. In another embodiment, the first and second mating structures each are made up of mating teeth structures.

The second mating structure 472 can be coupled to an interior surface of the handle housing 410, or the second mating structure 472 can be integrated in the structure of the handle housing 410. For example, in embodiments where the handle housing 410 is molded, the second mating structure 472 can also be defined by the mold. In this respect the second mating structure 472 can be plastic. In other embodiments the second mating structure 472 can be coupled to the handle housing 410 after formation of the handle housing 410 and/or the second mating structure 472. In such embodiments the second mating structure 472 can be coupled to the handle housing 410 through any suitable means known in the art.

The first and second springs in the embodiment shown in the FIGS. are wire coil springs. It is also possible to use springs of different configurations for one or both of the first and second springs, such as a flat spring or a wave spring.

Now referring to FIG. 9, it is possible to see the connections between the three parts of the wrench that make up the shaft: the shaft tip 426, the shaft mid-section 424 and the internal shaft 420. The components of the shaft do not rotate with respect to each other. However, it is possible for the other components of the wrench to rotate with respect to the shaft, under certain axial force or torque conditions, as discussed herein.

The components that make up the wrench can be constructed of a variety of materials known in the art, such as high density polyethylene, plastic, stainless steel, titanium, other metals and other materials. In one embodiment, the following components are made of metal, such as stainless steel: first spring, internal spring cap, second spring, internal shaft, shaft tip. In one embodiment, the following components are made of molded plastic, such as high density polyethylene: handle housing, end cap, slip component and shaft mid-section.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A wrench for coupling a set screw to a medical device comprising:
    a handle housing;
    a shaft comprising an interface section having a proximal end disposed within the handle housing and a distal end that is configured to be received in a set screw depression defined on a head of a set screw and an internal section disposed within the handle housing, the internal section of the shaft configured to engage the interface end of the shaft, the shaft defining an axis of the wrench;
    a first mating structure coupled to the internal section of the shaft;
    a second mating structure coupled to an interior surface of the handle housing, wherein the first and second mating structures are configured to engage one another, except when an axial force exceeding a first threshold is applied to the handle housing, the first mating structure disengages from the second mating surface allowing the handle housing to rotate with respect to the shaft;
    a first slip structure configured to engage the internal section of the shaft; and
    a second slip structure configured to engage the proximal end of the interface section of the shaft, wherein the first and second slip structures are configured to engage one another, except when torque applied to the handle housing exceeds a second threshold the first and second slip structures disengage allowing the handle housing to rotate with respect to the internal shaft.

2. The wrench of claim 1, wherein the wrench is configured so that if an axial force exceeding a warning threshold is applied to the handle housing, then tactile feedback will be provided to a user, where the warning threshold is less than the first threshold.

3. The wrench of claim 2, wherein the tactile feedback is axial movement of the handle housing with respect to the shaft.

4. The wrench of claim 1, further comprising:
    an internal spring cap disposed within the handle housing, wherein the internal spring cap is coupled to the interior section of the shaft; and
    a first spring positioned between an end of the handle housing and a first side of the internal spring cap.

5. The wrench of claim 1, wherein the internal spring cap is coupled in a fixed axial position with respect to an end of the shaft.

6. The wrench of claim 1, wherein the first mating structure defines at least one tapered notch and the second mating structure comprises at least one protrusion.

7. The wrench of claim 6, wherein the first mating structure defines four tapered notches and the second mating structure comprises four protrusions.

8. The wrench of claim 1, wherein the wrench is configured so that if torque exceeding a second threshold is applied to the handle housing, then the handle housing will rotate with respect to the shaft.

9. A system for coupling a set screw to a medical device comprising:
    a header assembly housing, the header assembly housing comprising a dielectric material, the header assembly further defining a set screw receptacle, the header assembly configured to receive a set screw for securing a lead to an electrode;
    a set screw comprising a head defining a depression;
    a wrench comprising:
        a handle housing;
        a shaft comprising an interface section having a proximal end disposed within the handle housing and a distal end that is configured to be received in the set screw depression and an internal section disposed within the handle housing, the internal section of the shaft configured to engage the interface end of the shaft, the shaft defining an axis,
        a first mating structure coupled to the shaft;
        a second mating structure coupled to an interior surface of the handle housing, wherein the first and second mating structures engage one another, except when an axial force exceeding a first threshold is applied to the handle housing, the first mating structure disengages from the second mating surface allowing the handle housing to rotate with respect to the shaft;
        a first slip structure configured to engage the internal section of the shaft; and
        a second slip structure configured to engage the proximal end of the interface section of the shaft, wherein the first and second slip structures are configured to engage one another, except when torque applied to the handle housing exceeds a second threshold the first and second slip structures disengage allowing the handle housing to rotate with respect to the internal shaft.

10. The wrench of claim 9, wherein the wrench is configured so that if an axial force exceeding a warning threshold is applied to the handle housing, then tactile feedback will be provided to a user, where the warning threshold is less than the first threshold.

11. The wrench of claim 10, wherein the tactile feedback is axial movement of the handle housing with respect to the shaft.

12. The system of claim 9, the header assembly housing defining a port aperture for receiving a connector pin of a stimulation lead, the port aperture having a first end and a second end.

13. The system of claim 9, further comprising a pulse generator housing coupled to header assembly housing.

14. The system of claim 9, further comprising:
   an internal spring cap within the handle housing, wherein the internal spring cap is coupled to the shaft; and
   a first spring positioned between an end of the handle housing and a first side of the internal spring cap.

15. The system of claim 14, wherein the internal spring cap is coupled in a fixed axial position with respect to an end of the shaft.

16. The wrench of claim 9, wherein the first mating structure defines four tapered notches and the second mating structure comprises four protrusions.

17. A method for coupling a set screw to a medical device comprising:
   providing a set screw comprising a head defining a depression;
   providing a wrench comprising:
      a shaft comprising an interface end that is configured to be received in the set screw depression, the shaft defining an axis, and
      a handle housing,
      a first mating structure coupled to the shaft;
      a second mating structure coupled to an interior surface of the handle housing, wherein the first and second mating structures fit together, except when an axial force exceeding a first threshold is applied to the handle housing, the first mating structure disengages from the second mating surface allowing the handle housing to rotate with respect to the shaft;
      a first slip structure configured to engage the internal section of the shaft; and
      a second slip structure configured to engage the proximal end of the interface section of the shaft, wherein the first and second slip structures are configured to engage one another, except when torque applied to the handle housing exceeds a second threshold the first and second slip structures disengage allowing the handle housing to rotate with respect to the internal shaft; and
   positioning the set screw within an opening in a medical device;
   placing the interface end of the wrench in the set screw depression; and
   rotating the wrench.

18. The method of claim 17, wherein the wrench is configured so that if an axial force exceeding a warning threshold is applied to the handle housing, then tactile feedback will be provided to a user, where the warning threshold is less than the first threshold.

* * * * *